United States Patent
Guerin et al.

(10) Patent No.: US 7,211,118 B2
(45) Date of Patent: May 1, 2007

(54) COMPOSITION FOR DYEING KERATIN FIBERS COMPRISING A DEFINED TRIHETEROYLMETHANE DIRECT DYE OR LEUCO PRECURSOR OF THIS DYE AND DYEING METHOD USING IT

(75) Inventors: Frédéric Guerin, Paris (FR); Alain Lagrange, Coupvray (FR)

(73) Assignee: L'Oreal S.A., Paris (FR)

( * ) Notice: Subject to any disclaimer, the term of this patent is extended or adjusted under 35 U.S.C. 154(b) by 58 days.

(21) Appl. No.: 10/746,497

(22) Filed: Dec. 29, 2003

(65) Prior Publication Data

US 2004/0194231 A1    Oct. 7, 2004

Related U.S. Application Data

(60) Provisional application No. 60/450,359, filed on Feb. 28, 2003.

(30) Foreign Application Priority Data

Dec. 30, 2002  (FR) .................................. 02 16849

(51) Int. Cl.
    *A61K 7/13* (2006.01)
(52) U.S. Cl. ...................... 8/405; 8/454; 8/565; 8/566; 8/567; 8/568; 8/569; 8/570; 8/571; 8/573; 8/574; 8/577
(58) Field of Classification Search .............. 8/405, 8/454, 565, 566, 567, 568, 569, 570, 571, 8/573, 574, 577
    See application file for complete search history.

(56) References Cited

U.S. PATENT DOCUMENTS

| | | |
|---|---|---|
| 3,418,117 A | 12/1968 | Becker |
| 3,423,427 A | 1/1969 | Cescon et al. |
| 3,627,893 A | 12/1971 | Seeger |
| 3,652,556 A | 3/1972 | Kuhlthau et al. |
| 3,685,956 A | 8/1972 | Raue et al. |
| 3,995,088 A | 11/1976 | Garner et al. ............. 428/323 |
| 4,054,718 A | 10/1977 | Garner et al. |
| 4,154,463 A | 5/1979 | Burri ........................ 282/27.5 |
| 4,254,032 A | 3/1981 | Petitpierre et al. ......... 260/315 |
| 4,340,540 A | 7/1982 | Hermann |
| 4,355,823 A * | 10/1982 | Burri ....................... 503/212 |
| 4,407,960 A | 10/1983 | Tratnyek |
| 4,460,385 A | 7/1984 | Pan et al. |
| 4,598,036 A | 7/1986 | Iwasaki et al. .......... 430/270 |
| 4,823,985 A | 4/1989 | Grollier et al. .............. 222/1 |
| 5,094,688 A | 3/1992 | Eckstein et al. |
| 5,097,034 A | 3/1992 | Eckstein |
| 5,266,699 A | 11/1993 | Naef et al. .................. 546/273 |
| 5,362,612 A | 11/1994 | Kiekens et al. ............. 430/520 |
| 5,708,151 A | 1/1998 | Möckli ........................ 534/608 |
| 5,733,343 A | 3/1998 | Möckli ........................ 8/426 |
| 5,888,252 A | 3/1999 | Möckli ........................ 8/405 |
| 2003/0066143 A1 | 4/2003 | Möckli ........................ 8/405 |

FOREIGN PATENT DOCUMENTS

| | | |
|---|---|---|
| BE | 702 240 | 2/1968 |
| DE | 1 248 193 | 10/1964 |
| DE | 1 569 750 | 4/1967 |
| DE | 1 254 118 | 5/1968 |
| DE | 1 620 564 | 5/1970 |
| DE | 1 569 749 | 1/1971 |
| DE | 29 17 271 | 11/1980 |
| EP | 0 714 954 A2 | 6/1996 |
| FR | 2 188 202 | 1/1974 |
| FR | 2 586 913 | 3/1987 |
| GB | 0 822 846 | 11/1959 |
| GB | 0 876 663 | 9/1961 |
| GB | 1 047 796 | 11/1966 |
| GB | 1 139 407 | 1/1969 |
| GB | 1 188 605 | 4/1970 |
| GB | 2 075 539 | 11/1981 |
| GB | 2 180 215 A | 3/1987 |
| JP | 59-162553 | 9/1984 |
| JP | 62-201967 | 9/1987 |

(Continued)

OTHER PUBLICATIONS

Barker et al., "Steric Effects in Di- and Tri-arylmethanes. Part IX.[1] Electronic Absorption Spectra of Julolidine (2,3,6,7-Tetrahydro-1$H$,5$H$-benzo[$ij$]quinolizine) and Kairoline (1-Methyl-1,2,3,4,-tetrahydroquinoline) Analogues of Michler's Hydrol blue, Malachite Green, Crystal Violet, and Michler's Ketone," J. Chem. Soc. (B), pp. 1068-71, 1969.

(Continued)

*Primary Examiner*—Eisa Elhilo
(74) *Attorney, Agent, or Firm*—Finnegan Henderson Farabow Garrett & Dunner LLP

(57) ABSTRACT

A composition for dyeing keratin fibers, such as human keratin fibers, and further such as the hair, comprising at least one dye chosen from heteroylmethane type direct dyes, such as triheteroylmethane direct dyes and leuco precursors of such dyes, as defined herein. A method that uses the composition for dyeing keratin fibers, such as human keratin fibers, and further such as the hair, and a kit or device containing same.

33 Claims, No Drawings

FOREIGN PATENT DOCUMENTS

| | | |
|---|---|---|
| JP | 8-179465 | 12/1996 |
| WO | WO 95/01772 | 1/1995 |
| WO | WO 95/15144 | 6/1995 |
| WO | WO 01/66646 A1 | 9/2001 |

OTHER PUBLICATIONS

French Search Report for priority application FR 02/16849.
English Abstract for FR 2 188 202.
Copending U.S. Appl. No. 10/745,634, filed Dec. 29, 2003.
Copending U.S. Appl. No. 10/746,501, filed Dec. 29, 2003.
English language Derwent Abstract of DE 1 254 118, May 22, 1968.
English language Derwent Abstract of DE 1 569 749, Jan. 21, 1971.
English language Derwent Abstract of DE 1 569 750, Jan. 21, 1971.
English language Derwent Abstract of DE 1 620 564, May 14, 1970.
English language Derwent Abstract of DE 29 17 271, Nov. 6, 1980.
English language Patent Abstracts of Japan Abstract of JP 59-162553, Sep. 13, 1984.
English language Derwent Abstract of JP 62-201967, Sep. 5, 1987.
English language Derwent Abstract of JP 8-179465, Dec. 7, 1996.
French Search Report of French Patent Application No. 0216845, dated Nov. 21, 2003.
French Search Report of French Patent Application No. 0216851, dated Oct. 8, 2003.
Office Action in co-pending U.S. Appl. No. 10/745,634, dated Oct. 20, 2005.
Office Action in co-pending U.S. Appl. No. 10/746,501, dated Oct. 20, 2005.
Shikhakiev: Izvestiya Vysshikh Uchebnykh Zavedenii, Khimiya I Khimicheskaya Tekhnologiya, vol. 42, No. 4, 1999, pp. 83-87.

* cited by examiner

COMPOSITION FOR DYEING KERATIN FIBERS COMPRISING A DEFINED TRIHETEROYLMETHANE DIRECT DYE OR LEUCO PRECURSOR OF THIS DYE AND DYEING METHOD USING IT

This application claims benefit of U.S. provisional application Ser. No. 60/450,359, filed Feb. 28, 2003.

An aspect of this disclosure relates to a composition for dyeing keratin fibers, such as human keratin fibers, and further such as the hair, that comprises at least one dye chosen from heteroylmethane type direct dyes, such as triheteroylmethane, and leuco precursors of them, as defined herein.

An aspect of this disclosure also relates to a method for dyeing keratin fibers, such as human keratin fibers and further such as hair that uses the composition.

There are many compositions and many methods for dyeing keratin fibers, such as human hair.

Thus, it is known that keratin fibers, such as human hair, can be dyed with dye compositions containing oxidation dye precursors, including ortho and paraphenylenediamines, ortho and para-aminophenols, heterocyclic compounds such as derivatives of diaminopyrazole, usually called "oxidation bases". Precursors of oxidation dyes, or oxidation bases, are colorless or slightly colored compounds that can be associated with oxidizing products to produce colored and coloring compounds through an oxidizing condensation process.

It is also known that the shades obtained with these oxidation bases can be varied by associating them with "couplers" or color modifiers, that are chosen, for example, from among aromatic metadiamines, meta-aminophenols, metadiphenols, and some heterocyclic compounds.

The variety of molecules involved, firstly in oxidation bases and secondly in couplers, makes it possible to obtain a wide range of colors.

"Permanent" coloration obtained using oxidation dyes can, moreover, satisfy at least one of a certain number of desirable characteristics, such as no toxicological disadvantages, possibility of giving shades in the desired intensity, and resistance to external agents, such as light, bad weather, washing, permanent waving, sweat, and rubbing.

According to one aspect of the present disclosure, the dyes can also cover white hair, and can be the least selective possible, making it possible to obtain the smallest possible coloring differences along the length of a keratin fiber that can in fact be sensitised differently. In other words, the fiber can be damaged between its end and its root leading to different sensitivities.

It can be seen that although conventional base-coupler combinations can be used to obtain a wide range of colors, they may not be able to satisfy at least one of the desirable characteristics listed above and may lead to the production of varied and poorly defined coupling products in the fiber, posing problems of safety and/or tenacity that can be difficult to control, as, for example, a selective color changing.

Another method of dyeing keratin fibers, such as the hair, is to use direct dyes.

Most conventional dyes used are chosen from nitrated benzenic, anthraquinonic, nitropyridinic, azoic, cationic azoic, xanthenic, azinic acridinic, triarylmethanic, nitrated benzenic type, and natural dyes.

These dyes, comprising colored and coloring molecules with an affinity for fibers, are applied to keratin fibers for a sufficiently long time to obtain the required color, and are then rinsed.

Consequently, direct dyes are now widely used since they also have some advantages compared with oxidation coloring precursors, such as reduction of potential allergy risks and lack of sensitization of the hair due to the oxidation process.

However, the colorations obtained can be temporary or semi-permanent, since the nature of the interactions that bind the direct dyes to the keratin fiber, and their desorption from the surface and/or the core of the fiber can be responsible for their low dyeing capacity and poor resistance to washing, bad weather, or sweat. These direct dyes are generally sensitive to light because of the low resistance of the chromophore to photochemical attack, in time leading to fading of the hair color.

Therefore, there is a need for a keratin fiber dye composition, for example, human keratin fibers such as the hair, that can have at least one of the following advantages: being safe, being totally compatible with keratin fibers, having low selectivity, providing a large variety of powerful colors, making it possible to obtain a fast and stable coloration of keratin fibers, and resisting external agents such as light, bad weather, washing, sweat, and rubbing, and also to subsequent treatments, such as permanent waving.

There is also a need for a dye composition for the treatment of all sorts of keratin fibers of all hair types, for example white hair, even if this hair has already been treated, for example with a bleaching or permanent waving treatment. Finally, there is a need for a composition that makes the coloring without it being necessary to firstly sensitise the keratin fiber of the hair.

An aspect of this disclosure is to provide a composition for dyeing keratin fibers, for example, human keratin fibers such as the hair, that among others satisfies at least one of the needs listed above.

Another aspect of this disclosure is also to supply a composition for dyeing keratin fibers without at least one of the inconveniences, defects, limitations, and disadvantages of the dye compositions of the prior art, whether it is a matter of dye compositions involving a coupler-base association or compositions involving a direct dye.

An aspect of the disclosure is a composition for dyeing keratin fibers, comprising, in a cosmetic medium suitable for dyeing, at least one dye chosen from formulae (I) and (II) given below, their tautomeric forms, and their addition salts:

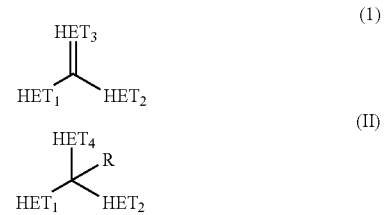

in which:

R is chosen from hydrogen, halogen; hydroxyl; alkoxy; and alkylthio;

$HET_1$, $HET_2$, $HET_3$ and $HET_4$, which may be identical or different, are chosen from heterocycle.

In formula (II) above, the term "alkyl" used for alkylthio radicals, and for groups comprising an alkyl part, means a straight or branched carbon chain comprising 1 to 30, such as from 1 to 8, and further such as from 1 to 4 carbon atoms, that can be carried and/or interrupted by at least one atom chosen from oxygen, sulphur, and nitrogen, that can be substituted with at least one group chosen from halogen, such as chlorine, bromine, iodine and fluorine; heterocycle; aryl; hydroxyl; alkoxy; amino; acyl; carboxamino; —$CO_2H$; $SO_3H$; —$PO_3H_2$; —$PO_4H_2$; —$NHSO_3H$; sulphonamide; monoalkylamino; trialkylammonium; and dialkylamino in which the two alkyl groups may form, together with the nitrogen atom of said dialkyl ($C_1$–$C_4$)amino group to which they are linked, a cycle that may be interrupted by at least one atom chosen from nitrogen, oxygen, and sulphur.

Similarly, unless otherwise mentioned, according to the disclosure, the term "alkoxy" used for alkoxy radicals means O-alkyl chains, the term alkyl having the meaning mentioned above. Acyl groups have, for example, 2 to 4 carbon atoms.

According to the disclosure, "heterocycle" means aromatic and non-aromatic cycles containing 5, 6 or 7 members, and from 1 to 3 heteroatoms chosen from nitrogen, sulphur, and oxygen. These heterocycles can be condensed on other heterocycles, or on other cycles, especially on aromatic cycles such as phenyl. They may be substituted with at least one substituent chosen from halogen; alkyl; alkoxy; hydroxyl; amino; alkylamino; and dialkylamino, in which the two alkyl groups may, together with the nitrogen atom to which they are linked, form a cycle that can be interrupted with at least one atom chosen from nitrogen, oxygen, and sulphur. These heterocycles may further be quaternized by an alkyl radical. The terms alkyl and alkoxy have the meanings described above.

According to an advantageous aspect of the disclosure, HET1 to HET4 are chosen from unsaturated heterocycle, such as aromatic heterocycle.

Among the heterocycle, such as those of HET1 to HET4, the following may be mentioned as examples: thiophene, benzothiophene, furan, benzofurane, indole, indoline, carbazole, pyridine, dehydroquinoleine, chromone, julolidine, thiadiazole, triazole, isoxazole, oxazole, thiazole, isothiazole, imidazole, pyrazole, triazine, thiazine, pyrazine, pyridazine, pyrimidine, pyridine, diazepine, oxazepine, benzotriazole, benzoxazole, benzimidazole, benzothiazole, morpholine, piperidine, piperazine, azetidine, pyrrolidine, and aziridine.

As disclosed herein, "aryl" means, unless otherwise mentioned, aryl that can be substituted with at least one substituent chosen from alkyl; alkoxy; acyl; cyano; carboxamido; —$CO_2H$; —$SO_3H$; —$PO_3H_2$; —$PO_4H_2$; hydroxyl; amino; monoalkyl($C_1$–$C_4$)amino; and dialkyl($C_1$–$C_4$)amino, in which the two alkyl groups may form, together with the nitrogen atom in the dialkyl($C_1$–$C_4$)amino group to which they are linked, a cycle that may be interrupted by at least one atom chosen from nitrogen, oxygen, and sulphur. For example, aryl is chosen from phenyl and naphthyl that may be substituted as mentioned above.

Dyes (I) can be defined as being direct dyes of the triheteroylmethane type and dyes of formula (II) are leuco precursors of the triheteroylmethanes of formula (I), and as used herein are also referred to as dyes.

Leuco dyes (II) are usually only slightly colored or are not colored at all and can be converted by simple oxidation in air or in the presence of an oxidizing agent into a triheteroylmethane compound of formula (I).

Examples of dyes of formula (I) and (II) useful as dyes in the dye compositions according to the disclosure, are the following compounds for which the counter ions are specified or not specified, and their addition salts:

1H-Benzo[ij]quinolizinium, 9-[bis(2,3,6,7-tetrahydro-1H,5-H-benzo[ij]quinolizin-9-yl)methylene]-2,3,5,6,7,9-hexahydro-chloride;

5H-Benzo[a]carbazolium, 11-ethyl-5-[(11-ethyl-11H-benzo[a]carbazol-5-yl)(1-ethyl-1,2,3,4-tetrahydro-5-quinolinyl)methylene]-;

Pyrrolo[3,2,1-ij]quinolinium, 8-[bis(1,2,5,6-tetrahydro-4H-pyrrolo[3,2,1-ij]quinolin-8-yl)methylene]-1,2,4,5,6,8-hexahydro-;

Tri(9-ethy-9H-carbazol-3-yl)methane;

Bis(6-Chloro-9-ethy-9H-carbazol-3-yl)-(9-ethy-9H-carbazol-3-yl)methane;

Bis(1-(4-sulfo-butyl)-2,3,4,6-tetrahydro-quinolinium)-pyrid-4-yl-methane;

Bis(1-ethyl-2-methyl-1H-indol-3-yl)-(9-ethy-9H-carbazol-3-yl)methane;

Tri(7-ethyl-7H-benzo[c]carbazol-10-yl)methane;

Bis((6-dimethylamino-3-methyl-1H-indol-2-yl)-2-furyl-methane;

Bis((6-dimethylamino-3-methyl-1H-indol-2-yl)-(pyrid-4-yl)methane;

Bis(1-ethyl-2-methyl-1H-indol-3-yl)-2-thienylmethane;

3-[(1-ethyl-2-methyl-1H-indol-3-yl)-(9-ethy-9H-carbazol-3-yl) methylene]-1-ethyl-2-methyl-3H-indolium; and 3-[(1-ethyl-2-methyl-1H-indol-3-yl)-2-thienyl)methylene]-1-ethyl-2-methyl-3H-indolium.

Triheteroylmethanes of formula (I) and leuco dyes of formula (II) are known compounds. These compounds may be prepared according to synthesis processes well known in the literature and as described, for example, in documents FR-A-2 188 202, U.S. Pat. No. 3,995,088, U.S. Pat. No. 4,154,463, U.S. Pat. No. 4,254,032, U.S. Pat. No. 4,355,823, U.S. Pat. No. 5,266,699 and U.S. Pat. No. 5,362,612, all of which are herein incorporated by reference in their entireties.

It is found that, surprisingly, at least some compositions according to the disclosure make it possible to obtain intense colors, even on non-sensitised hair.

A variety of chromatic or dark, very bright, only slightly selective and durable glints can be obtained with compositions according to the disclosure.

Thus, with the triheteroylmethane dyes of formula (I) and the leucos of formula (II) included in the compositions according to the disclosure any shade from green to blue, passing through red and in particular black shades can be obtained (after revelation for leuco compounds (II)).

Colorations obtained with compositions according to the disclosure can be at least one of durable, stable, and resistant to bad weather, washing, sweat, rubbing, and subsequent treatments such as permanent wavings.

In particular, these colorations can be resistant to light.

The at least one dye of formulae (I) and (II) above and/or their tautomeric forms and addition salt(s) usually represent from about 0.0001 to about 10% by weight of the total weight of the dye composition, such as from about 0.005 to about 10% by weight and further such as from about 0.01 to about 6% by weight of the total weight of the dye composition according to the disclosure.

The dye composition according to the disclosure may also contain at least one direct dye different from the dyes of formulae (I) and (II). The at least one different direct dye may, for example, be chosen from neutral, acid, and cationic benzenic nitrated direct dyes, neutral, acid, and cationic azoic dyes, quinonic direct dyes, such as neutral, acid, and cationic anthraquinones, azinic direct dyes, triarylmethanic direct dyes, indoaminic direct dyes, and natural direct dyes.

Among the benzenic direct dyes the following compounds may cited in a non-limitative manner:
1,4-diamino-2-nitrobenzene;
1-amino-2 nitro-4-β-hydroxyethylaminobenzene;
1-amino-2 nitro-4-bis(β-hydroxyethyl)-aminobenzene;
1,4-Bis(β-hydroxyethylamino)-2-nitrobenzene;
1-β-hydroxyethylamino-2-nitro-4-bis-(β-hydroxyethylamino)-benzene;
1-β-hydroxyethylamino-2-nitro-4-aminobenzene;
1-β-hydroxyethylamino-2-nitro-4-(ethyl)(β-hydroxyethyl)-aminobenzene;
1-amino-3-methyl-4-β-hydroxyethylamino-6-nitrobenzene;
1-amino-2-nitro-4-β-hydroxyethylamino-5-chlorobenzene;
1,2-Diamino-4-nitrobenzene;
1-amino-2-β-hydroxyethylamino-5-nitrobenzene;
1,2-(β-hydroxyethylamino)-4-nitrobenzene;
1-amino-2-tris-(hydroxymethyl)-metylamino-5-nitrobenzene;
1-Hydroxy-2-amino-5-nitrobenzene;
1-Hydroxy-2-amino-4-nitrobenzene;
1-Hydroxy-3-nitro-4-aminobenzene;
1-Hydroxy-2-amino-4,6-dinitrobenzene;
1-β-hydroxyethyloxy-2-β-hydroxyethylamino-5-nitrobenzene;
1-Methoxy-2-β-hydroxyethylamino-5-nitrobenzene;
1-β-hydroxyethyloxy-3-methylamino-4-nitrobenzene;
1-β,γ-dihydroxypropyloxy-3-methylamino-4-nitrobenzene;
1-β-hydroxyethylamino-4-β,γ-dihydroxypropyloxy-2-nitrobenzene;
1-β,γ-dihydroxypropyloxy-4-trifluoromethyl-2-nitrobenzene;
1-β-hydroxyethylamino-4-trifluoromethyl-2-nitrobenzene;
1-β-hydroxyethylamino-3-methyl-2-nitrobenzene;
1-β-aminoethylamino-5-methoxy-2-nitrobenzene;
1-hydroxy-2-chloro-6-ethylamino-4-nitrobenzene;
1-hydroxy-2-chloro-6-amino-4-nitrobenzene;
1-hydroxy-6-bis-(β-hydroxyethyl)-amino-3-nitrobenzene;
1-β-hydroxyethylamino-2-nitrobenzene; and
1-Hydroxy-4-β-hydroxyethylamino-3-nitrobenzene.

Representative azoic direct dyes include cationic azoic dyes described in patent applications WO 95/15144, WO-95/01772, EP-714954 and WO-A-01/66646, the disclosures of which related to azoic direct dyes is specifically incorporated by reference herein.

Among these compounds, note particularly the following dyes:
1,3-dimethyl-2-[[4-(dimethylamino)phenyl]azo]-1H-Imidazolium chloride;
1,3-dimethyl-2-[[4-(aminophenyl]azo]-1H-Imidazolium chloride;
1-methyl-4-[(methylphenylhydrazono)methyl]-pyridinium methylsulfate.

The following dyes described in the COLOR INDEX INTERNATIONAL 3rd EDITION may also be cited among the azoic direct dyes:
Disperse Red 17;
Acid Yellow 9;
Acid Black 1;
Basic Red 22;
Basic Red 76;
Basic Yellow 57;
Basic Brown 16;
Acid Yellow 36;
Acid Orange 7;
Acid Red 33;
Acid Red 35;
Basic Brown 17;
Acid Yellow 23;
Acid Orange 24;
Disperse Black 9.
1-(4'-aminodiphenylazo)-2-methyl-4bis-(β-hydroxyethyl)aminobenzene and 4-hydroxy-3-(2-methoxyphenylazo)-1-naphthalene sulphonic acid may also be cited.

The following dyes may be cited among quinonic direct dyes:
Disperse Red 15;
Solvent Violet 13;
Acid Violet 43;
Disperse Violet 1;
Disperse Violet 4;
Disperse Blue 1;
Disperse Violet 8;
Disperse Blue 3;
Disperse Red 11;
Acid Blue 62;
Disperse Blue 7;
Basic Blue 22;
Disperse Violet 15; and
Basic Blue 99, as well as the following compounds:
1-N-methylmorpholiniumpropylamino-4-hydroxyanthraquinone;
1-Aminopropylamino-4-methylaminoanthraquinone;
1-Aminopropylaminoanthraquinone;
5-hydroxyethyl-1,4-diaminoanthraquinone;
2-Aminoethylaminoanthraquinone; and
1,4-Bis-(β-γ-dihydroxypropylamino)-anthraquinone.

The following compounds may be cited among the azinic dyes:
Basic Blue 17; and
Basic Red 2.

The following compounds may be cited among the triarylmethanic dyes:
Basic Green 1;
Acid Blue 9;
Basic Violet 3;
Basic Violet 14;
Basic Blue 7;

Acid Violet 49;
Basic Blue 26; and
Acid Blue 7.

The following compounds may be cited among the indoaminic dyes:

2-β-hydroxyethylamino-5-[bis-(β-4'-hydroxyethyl)amino] anilino-1,4-benzoquinone;
2-β-hydroxyethylamino-5-(2'-methoxy-4'-amino)anilino-1, 4-benzoquinone;
3-N(2'-Chloro-4'-hydroxy)phenyl-acetylamino-6-methoxy-1,4-benzoquinone imine;
3-N(3'-Chloro-4'-methylamino)phenyl-ureido-6-methyl-1, 4-benzoquinone imine; and
3-N[4'-N-(Ethyl, carbamylmethyl)amino]phenyl-ureido-6-methyl-1,4-benzoquinone imine.

Representative natural direct dyes include: lawsone, juglone, alizarine, purpurine, carminic acid, kermesic acid, purpurogalline, protocatechaldehyde, indigo, isatine, curcumine, spinulosine and apigenidine, extracts and decoctions containing these natural dyes, and, for example, cataplasms and henna based extracts can also be used.

The additional at least one direct dye different from dyes of formulae (I) and (II), their tautomeric forms, and addition salts represent, for example, from about 0.001 to about 20% by weight of the total weight of the composition when ready to use and for example, from about 0.005 to about 10% by weight.

According to the present disclosure, the composition may further comprise at least one oxidation base and optionally at least one coupler, such as those conventionally used for oxidation dyeing.

Examples of oxidation bases include paraphenylenediamines, bisphenylalkylenediamines, para-aminophenols, ortho-aminophenols, heterocyclic bases, and their addition salts.

For example, couplers may include metaphenylenediamine couplers, meta-aminophenol couplers, metadiphenol couplers, naphthalenic couplers, heterocyclic couplers, and their addition salts.

When present, the at least one oxidation base and at least one coupler are each usually present in an amount ranging from about 0.001 to about 10% by weight, such as from about 0.005 to about 6% by weight, of the total weight of the dye composition.

The medium suitable for dyeing, also called the dye support, is generally chosen from water and a mixture of water and at least one organic solvent to solubilise compounds that would not be sufficiently water-soluble. Some examples of organic solvents are the lower alkanols in $C_1$–$C_4$, such as ethanol and isopropanol; polyols and polyol ethers such as 2-butoxyethanol, propyleneglycol, propyleneglycol monomethylether, diethyleneglycol monoethylether and monoethylether, and aromatic alcohols, such as benzylic alcohol and phenoxythanol, and mixtures thereof.

The solvents may be present in proportions, for examples, ranging from about 1 to about 40% by weight based on the total weight of the dye composition, such as from about 5 to about 30% by weight.

According to the present disclosure, the dye composition may also contain various additives conventionally used in compositions for dyeing the hair, such as anionic, cationic, non-ionic, amphoteric, and zwitterionic surfactants, and mixtures of these surfactants, anionic, cationic, non-ionic, amphoteric, and zwitterionic polymers and mixtures of these polymers, mineral and organic thickeners, such as anionic, cationic, non-ionic and amphoteric polymer associative thickeners, antioxidants, penetration agents, sequestering agents, fragrances, buffers, dispersants, conditioning agents, such as modified and non-modified volatile and non-volatile silicones, film-forming agents, ceramides, preservatives, and opacifiers.

For example, the above additives are usually present each in an amount ranging from about 0.01 to about 20% based on the total weight of the composition.

For example, the compositions contain a solvent chosen from $C_2$–$C_4$ alkanols and polyols with a molecular weight of less than about 1000.

The compositions can, for example, contain at least one surfactant and/or at least one thickening agent chosen from mineral and organic thickeners.

Obviously, one skilled in the art will take care to choose additives so that at least one advantageous property intrinsically attached to the oxidation dye composition according to the disclosure is not modified or is not substantially modified by the envisaged additive(s).

The pH of the dye composition according to the disclosure, for example, usually ranges from about 3 to about 12, such as from about 5 to about 11, and further such as from about 6 to about 8.5.

The pH can be adjusted to the required value by acidifying agents and alkalising agents usually used for dyeing keratin fibers, as well by using conventional buffer systems.

Exemplary acidifying agents include, for example, mineral and organic acids, such as hydrochloric acid, orthophosphoric acid, sulphuric acid, carboxylic acids, like acetic acid, tartric acid, citric acid, and lactic acid, and sulfonic acids.

Exemplary alkalizing agents include, for example, ammonia, alkaline carbonates, alkanolamines, such as mono-, di- and triethanolamines and their derivatives, sodium and potassium hydroxide, and compounds of formula (III):

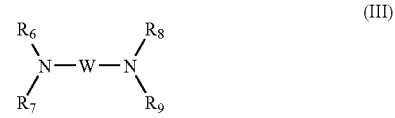

(III)

wherein W is a propylene moiety optionally substituted with at least one substituent chosen from hydroxyl and alkyl $C_1$–$C_4$; $R_6$, $R_7$, $R_8$ and $R_9$ which can be identical or different, are chosen from hydrogen, alkyl $C_1$–$C_4$, and hydroxyalkyl $C_1$–$C_4$.

The dye composition according to the disclosure may be in various forms, such as in the form of liquids, creams, gels or in any other suitable form to achieve dyeing of keratin fibers, such as the human hair.

An aspect of the disclosure is also a method for the direct dyeing of keratin fibers, for example human keratin fibers such as the hair, that includes the application of at least one dye composition comprising at least one dye of formula (I) and (II), their tautomeric forms, and their addition salts as defined above on keratin fibers. After a pause time, the keratin fibers are rinsed allowing colored fibers to appear. The pause time (exposure time) usually ranges from about 3 to 50 minutes, such as from about 5 to about 30 minutes.

By direct coloring or dyeing (tinting) it is meant that dyeing is carried out without an oxidant other than the oxygen in the air.

When the dyeing composition comprises at least one compound of formula (II) or at least one compound of formula (I) and at least one oxidation base, and optionally one or several couplers, the dye composition may contain an oxidant.

Therefore, another aspect of the disclosure is a method for dyeing keratin fibers, for example, human keratin fibers such as the hair, comprising applying to the fibers a composition for dyeing fibers comprising, in a cosmetic medium suitable for dyeing, at least one dye chosen either from formula (II), its tautomeric forms, and its acid addition salts, or from formula (I), its tautomeric forms, and its acid addition salts, and at least one oxidation base and optionally at least one coupler, and developing with at least one oxidizing agent the color at acid, neutral or alkaline pH.

Representative oxidizing agents include, for example hydrogen peroxide, urea peroxide, alkaline metal bromates, persalts such as perborates and persulfates, peracids and oxidase enzymes including peroxidases, oxydo-reductases with two electrons such as uricases and oxygenases with four electrons such as laccases. Hydrogen peroxide can be used, for example.

The oxidizing agent may be added to the composition according to the disclosure just at the time of use or it may be added starting from an oxidizing composition containing it, applied simultaneously or sequentially with the composition according to the disclosure. The oxidizing composition may also contain various additives conventionally used in compositions for dyeing the hair and as defined herein.

If the oxidizing composition is mixed with the dye composition, the pH of the oxidising composition containing the oxidizing agent is such that after mixing with the dye composition, the pH of the resulting composition applied on the keratin fibers varies, for example, from about 3 to about 12, such as from about 5 to about 11, and further such as from about 6 to about 8.5. The pH may be adjusted to the desired value by acidifying agents and alkalinizing agents usually used in the dyeing of keratin fibers and as defined herein.

The composition that is finally applied on the keratin fibers may be in various forms, such as liquids, creams or gels or any other appropriate form for dyeing keratin fibers, such as human hair.

Another aspect of the disclosure is a device or kit with several compartments, sometimes called a dyeing "kit" in which a first compartment containing at least one dye chosen either from formula (II), its tautomeric forms, and its addition salts, or formula (I), its tautomeric forms, and its addition salts, and at least one oxidation base and optionally at least one coupler, and a second compartment containing an oxidizing composition.

This device may be equipped with a device for delivering the desired mixture on the hair, such as devices described in patent FR-2 586 913 to the applicant.

In the case of a composition containing at least one dye chosen from formula (II), its tautomeric forms, and its addition salts, it is desirable to avoid contact between said at least one dye and oxygen in the air. To this end, an aerosol device can then be one suitable packaging mode.

With the dyes according to the disclosure, direct lightening dyeing is also possible in the absence of oxidation dyes and in the presence of an oxidizing agent in such conditions (for example hydrogen peroxide in an alkaline medium) so that this oxidizing agent can bleach, i.e., make the keratin fibers lighter, by action on pigments initially present in the fibers.

The following examples illustrate the invention, although they are in no way restrictive.

EXAMPLE 1

The following dye composition was prepared:

Compound 1

| | |
|---|---|
| 3-[(1-ethyl-2-methyl-1H-indol-3-yl)-(9-ethyl-9H-carbazol-3-yl)methylene]-1-ethyl-2-methyl-3H-indolium chloride | 0.56 g |
| Benzylic alcohol | 4.0 g |
| Polyethyleneglycol 60E | 6.0 g |
| Hydroxyethylcellulose | 0.7 g |

-continued

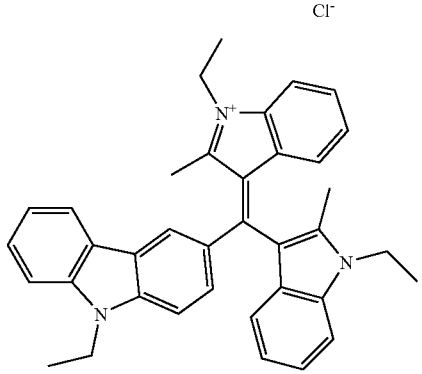

Compound 1

| | | |
|---|---|---|
| Alkylpolyglucoside in aqueous solution at 60% M.A.* | | 4.5 g M.A. |
| Phosphate buffer | q.s | pH7 |
| Deionised water | q.s | 100.00 g |

*Active Matter

The above composition was applied to locks of natural grey hair or permed hair containing 90% white hair, and was allowed to stand for 20 minutes. After rinsing with running water and drying, the hair was dyed with a red shade.

EXAMPLE 2

The following dye composition was prepared:

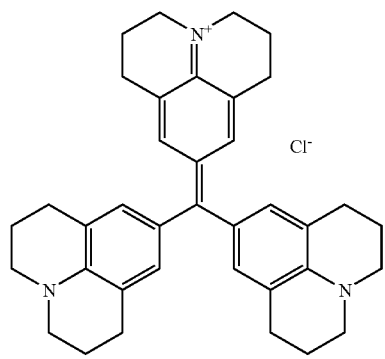

Compound 2

| | | |
|---|---|---|
| 1H-Benzo[l, j]quinolizinium, 9-[bis(2,3,6,7-tetrahydro-1H, 5H-benzo[l, j]quinolizin-9-yl)methylene]-2,3,5,6,7,9-hexahydro chloride-($10^{-3}$ mole) | | 0.55 g |
| Oleic diethanolamine | | 3 g |
| Lauric acid | | 1 g |
| Ethyleneglycol monoethylether | | 5 g |

-continued

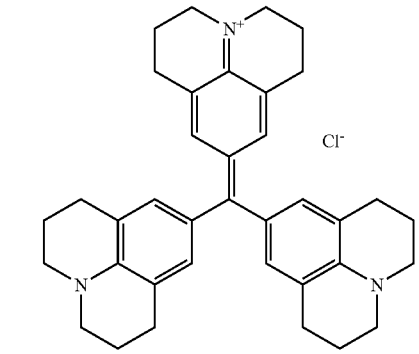

Compound 2

| | | |
|---|---|---|
| Hydroxyethylcellulose | | 2 g |
| 2-amino-2-methyl-1-propanol | q.s | pH9.5 |
| Deionised water | q.s | 100 g |

The above composition was applied to locks of natural grey hair or permanent-waved hair containing 90% white hair, and was allowed to stand for 30 minutes. After rinsing with running water and drying, the hair was dyed with a blue shade.

EXAMPLES 3 TO 6

The direct dye compositions defined in the following table were prepared (all contents are expressed in grams):

| Compound 1 | Compound 2 |
|---|---|
| 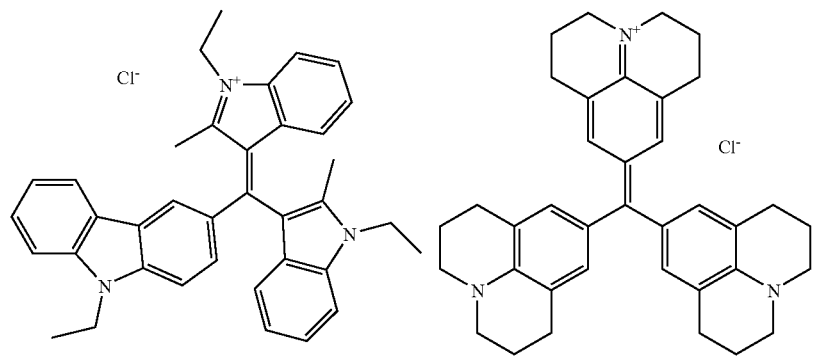 | |
| 3-[(1-ethyl-2-methyl-1H-indol-3-yl)-(9-ethyl-9H-carbazol-3-yl)methylene]-1-ethyl-2-methyl-3H-indolium chloride | 1H-Benzo[ij]quinolizinium, 9-[bis(2,3,6,7-tetrahydro-1H,5H-benzo[ij]quinolizin-9-yl)methylene]-2,3,5,6,7,9-hexahydro chloride |

| Compound 3 | Compound 4 |
|---|---|
| 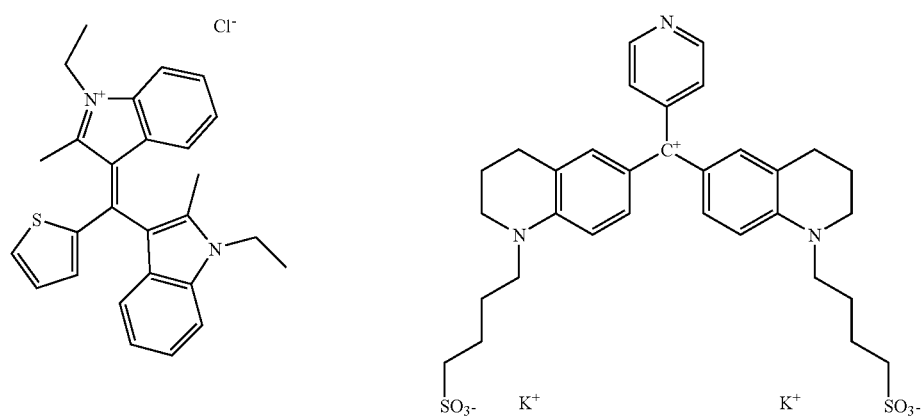 | |
| 3-[(1-ethyl-2-methyl-1H-indol-3-yl)-2-thienyl)methylene]-1-ethyl-2-methyl-3H-indolium chloride | Bis(1-(4-sulfobutyl)-2,3,4,6-tetrahydro-quinolinium)-pyrid-4-yl-methane dipotassium salt |

| | Example 3 | Example 4 | Example 5 | Example 6 |
|---|---|---|---|---|
| Direct dye formula (1) | 0.2 | | | |
| Direct dye formula (2) | | 0.2 | | |
| Direct dye formula (3) | | | 0.2 | |
| Direct dye formula (4) | | | | 0.2 |
| Cross-linked polyacrylic acid sold by the Goodrich company under the name Carbopol 2984 | 1.0 MA* | | | |
| Ammonium acrylate/acrylamide copolymer sold by the Hoechst company under the name Bozepol C Nouveau (New) | | 1.0 MA* | | |
| Cross-linked methacrylic acid/ethyl acrylate copolymer sold in aqueous dispersion with 38% active matter by the Coatex under the name Viscoatex 538C | | | 1.0 MA* | |
| Cross-linked acrylic acid/ethyl acrylic copolymer in aqueous dispersion with 28% active matter by the Rohm & Haas Company under the name Aculyn 33 | | | | 1.0 MA* |
| Ethanol | 10 | 10 | 10 | 10 |
| 2-amino-2-methyl-1-propanol   qs | pH 9 | pH 9 | pH 9 | pH 9 |
| Deionised water   qs | 100 | 100 | 100 | 100 |

MA* denotes Active Matter

The above compositions were applied for 30 minutes each on locks of natural grey hair with 90% white hair. The strands of hair were then rinsed, washed with a standard shampoo, and then dried.

The strands were dyed in the following shades:

| Examples | Shade obtained |
|---|---|
| 3 | Bright red |
| 4 | Bright blue |
| 5 | Bright orange |
| 6 | Bright blue |

EXAMPLES 7 TO 10

Compositions 7 (A) to 10 (A) were prepared according to the invention, as follows (contents in grams):

| COMPOSITION | 7 (A) | 8 (A) | 9 (A) | 10 (A) |
|---|---|---|---|---|
| Paratoluylenediamine | 0.25 | — | — | — |
| Para-aminophenol | 0.30 | 0.50 | 0.15 | — |
| Paraphenylenediamine | — | 0.20 | — | 0.30 |
| 5-N-(β-hydroxyethyl) amino 2-methyl phenol | 0.5 | 0.8 | 0.17 | — |
| 5-amino 2-methyl phenol | — | — | — | 0.30 |
| Dye of structure (2) | 0.15 | — | — | — |
| Dye of structure (3) | — | 0.20 | 0.05 | — |
| Dye of structure (4) | — | — | — | 0.1 |
| Common tint support (*) | (*) | (*) | (*) | (*) |
| Water q.s. | 100 g | 100 g | 100 g | 100 g |

(*) The common dye support comprised the following composition:

| | |
|---|---|
| Polyglycerolated oleic acid with 2 moles of glycerol | 4.0 g |
| Polyglycerolated oleic acid with 4 moles of glycerol, and 78% of active matters (M.A.) | 5.69 g M.A. |
| Oleic acid | 3.0 g |
| Oleic amine with 2 moles of ethylene oxide sold under the commercial name ETHOMEEN O12 by the AKZO company | 7.0 g |
| Diethylaminopropyllaurylaminosuccinamate, sodium salt with 55% M.A. | 3.0 g M.A. |
| Oleic alcohol | 5.0 g |
| Oleic acid diethanolamine | 12.0 g |
| Propyleneglycol | 3.5 g |
| Ethyl alcohol | 7.0 g |
| Dipropyleneglycol | 0.5 g |
| Prolyleneglycol monomethylether | 9.0 g |
| Sodium metabisulfite in aqueous solution, with 35% M.A. | 0.455 g MA |
| Ammonium acetate | 0.8 g |
| Anti-oxidant, sequestering agent | q.s. |
| Fragrance, preservative | q.s. |
| Ammonia with 20% NH$_3$ | 10.0 g |

At the time of use, each of these compositions 7(A) to 10(A) was mixed with an equal quantity of a composition (B) comprising a solution of hydrogen peroxide 20 volumes (6% by weight).

Each resulting composition (ready-to-use composition according to the disclosure) was applied for 30 minutes to locks of natural grey hair with 90% white. The hair locks were then rinsed, washed with a standard shampoo, and then dried.

The hair strands were dyed in the shades shown in the following table:

| EXAMPLE [COMPOSITION] | SHADE OBTAINED |
|---|---|
| 7 [7(A)] | Dark blond with blue glints |
| 8 [8(A)] | Blond with orange glints |
| 9 [9(A)] | Light blond with orange glints |
| 10 [10(A)] | Blond with blue glints |

The shades obtained have very good resistance to subsequent shampoos.

According to one variant of the disclosure, direct dyes with structures (2), (3) and (4) may be incorporated in the dyeing compositions 7 (A), 8 (A), 9 (A) and 10 (A) at the time of use.

EXAMPLE 11

The following composition 11 (A) was prepared:

| | |
|---|---|
| 1,4-diamino benzene | 0.40 g |
| 5-amino 2-methyl phenol | 0.45 g |
| Common dye support as described previously for application examples 7 to 10 | (*) |
| ionised water q.s. | 100 g |

The following composition 11 (A') was prepared:

Compound 5

| | |
|---|---|
| Cationic dye Bis(1-ethyl-2-methyl-1H-indol-3-yl)-2-thienylmethane | 4 g |
| Quaternary polyammonium sold by the National Starch Company under the commercial name CELQUAT SC-240 | 10 g |
| Wood sawdust q.s. | 100 g |

At the time of use, one part by weight of composition 11 (A) above was mixed with 0.1 part by weight of composition 11 (A') and with one part by weight of a composition (B) comprising a solution of hydrogen peroxide 20 volumes (6% by weight).

The resulting composition was applied onto locks of natural grey hair with 90% white, for 30 minutes. The hair was then rinsed, washed with a standard shampoo, and then dried.

The hair was dyed in a light auburn shade with orange glints that resists subsequent washings very well.

What is claimed is:

1. A composition for dyeing human keratin fibers, comprising:
   a cosmetic medium suitable for dyeing human keratin fibers, wherein said medium is water or a mixture of water and at least one organic solvent, and
   at least one dye comprised in said medium and chosen from formulae (I) and (II), their tautomeric forms, and their addition salts:

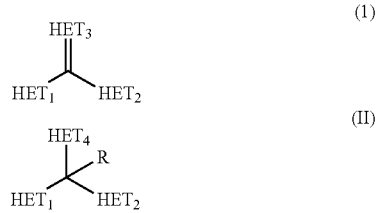

in which:
   R is chosen from hydrogen, halogen; hydroxyl; alkoxy, and alkylthio; and
   $HET_1$, $HET_2$, $HET_3$ and $HET_4$, which may be identical or different, are chosen from heterocycles.

2. A dye composition according to claim 1, wherein the $HET_1$ to $HET_4$ are chosen from unsaturated heterocycles.

3. A dye composition according to claim 2, wherein the $HET_1$ to $HET_4$ are chosen from aromatic heterocycles.

4. A dye composition according to claim 1, wherein the heterocycles are chosen from thiophene, benzothiophene, furan, benzofurane, indole, indoline, carbazole, pyridine, dehydroquinoleine, chromone, julolidine, thiadiazole, triazole, isoxazole, oxazole, thiazole, isothiazole, imidazole, pyrazole, triazine, thiazine, pyrazine, pyridazine, pyrimidine, pyridine, diazepine, oxazepine, benzotriazole, benzoxazole, benzimidazole, benzothiazole, morpholine, piperidine, piperazine, azetidine, pyrrolidine, and aziridine.

5. A dye composition for dyeing keratin fibers, comprising, in a cosmetic medium suitable for dyeing, at least one dye chosen from the following compounds, for which the counter ions are specified or not specified, and their addition salts:
   1H-Benzo[ij]quinolizinium, 9-[bis(2,3,6,7-tetrahydro-1H,5H-benzo[ij]quinolizin-9-yl)methylene]-2,3,5,6,7,9-hexahydro-chloride;
   5H-Benzo[a]carbazolium, 11-ethyl-5-[(11-ethyl-11H-benzo[a]carbazol-5-yl)(1-ethyl-1,2,3,4-tetrahydro-5-quinolinyl)methylene]-;
   Pyrrolo[3,2,1-ij]quinolinium, 8-[bis(1,2,5,6-tetrahydro-4H-pyrrolo[3,2,1-ij]quinolin-8-yl)methylene]-1,2,4,5,6,8-hexahydro-;
   Tri(9-ethyl-9H-carbazol-3-yl)methane;
   Bis(6-Chloro-9-ethy-9H-carbazol-3-yl)-(9-ethyl-9H-carbazol-3-yl)methane;
   Bis(1-(4-sulfo-butyl)-2,3,4,6-tetrahydro-quinolinium)-pyrid-4-yl-methane;
   Bis(1-ethyl-2-methyl-1H-indol-3-yl)-(9-ethyl-9H-carbazol-3-yl)methane;
   Tri(7-ethyl-7H-benzo[c]carbazol-10-yl)methane;
   Bis((6-dimethylamino-3-methyl-1H-indol-2-yl)-2-furylmethane;
   Bis((6-dimethylamino-3-methyl-1H-indol-2-yl)-(pyrid-4-yl)methane;
   Bis(1-ethyl-2-methyl-1H-indol-3-yl)-2-thienylmethane;
   3-[(1-ethyl-2-methyl-1H-indol-3-yl)-(9-ethy-9H-carbazol-3-yl) methylene]-1-ethyl-2-methyl-3H-indolium; and
   3-[(1-ethyl-2-methyl-1H-indol-3-yl)-2-thienyl)methylene]-1-ethyl-2-methyl-3H-indolium.

6. A dye composition according to claim 1, wherein the at least one dye is present in an amount ranging from about 0.0001 to about 10% by weight of the total weight of the dye composition.

7. A dye composition according to claim 6, wherein the at least one dye is present in an amount ranging from about 0.005 to about 10% by weight of the total weight of the dye composition.

8. A dye composition according to claim 7, wherein the at least one dye is present in an amount ranging from about 0.01 to about 6% by weight of the total weight of the dye composition.

9. A dye composition according to claim 1, further comprising at least one direct dye different from the at least one dye chosen from formulae (I) and (II), their tautomeric forms, and their addition salts.

10. A dye composition according to claim 9, wherein the at least one direct dye different from the at least one dye chosen from formulae (I) and (II), their tautomeric forms, and their addition salts is chosen from neutral, acid, and cationic benzenic nitrated direct dyes, neutral, acid, and cationic azoic dyes, quinonic direct dyes, azinic direct dyes, triarylmethanic direct dyes, indoaminic direct dyes, and natural direct dyes.

11. A dye composition according to claim 10, wherein the quinonic direct dyes are chosen from neutral, acid, and cationic anthraquinones.

12. A dye composition according to claim 10, wherein the at least one direct dye different from the at least one dye chosen from formulae (I) and (II), their tautomeric forms, and their addition salts is present in an amount from about 0.001 to about 20% by weight of the total weight of the dye composition.

13. A dye composition according to claim 12, wherein the at least one direct dye different from the at least one dye chosen from formulae (I) and (II), their tautomeric forms, and their addition salts is present in an amount ranging from about 0.005 to about 10% by weight of the total weight of the dye composition.

14. A dye composition according to claim 1, further comprising at least one oxidation base and optionally at least one coupler.

15. A dye composition according to claim 14, wherein said at least one oxidation base is chosen from paraphenylenediamines, bisphenylalkylenediamines, para-aminophenols, ortho-aminophenols, heterocyclic bases, and their addition salts.

16. A dye composition according to claim 14, wherein said at least one coupler is chosen from metaphenylenediamine couplers, meta-aminophenol couplers, metadiphenol couplers, naphthalenic couplers, heterocyclic couplers, and their addition salts.

17. A dye composition according to claim 14, wherein said at least one oxidation base and said at least one optional coupler are each present in an amount ranging from about 0.001 to about 10% by weight, of the total weight of the dye composition.

18. A dye composition according to claim 14, wherein said at least one oxidation base and said at least one optional coupler are each present in an amount ranging from about 0.005 to about 6% by weight, of the total weight of the dye composition.

19. A dye composition according to claim 1, having a pH ranging from about 3 to about 12.

20. A dye composition according to claim 19, having a pH ranging from about 5 to about 11.

21. A dye composition according to claim 20, having a pH ranging from about 6 to about 8.5.

22. A method for the direct dyeing of keratin fibers, comprising:

applying to said fibers a composition for dyeing keratin fibers, comprising, in a cosmetic medium suitable for dyeing, at least one dye chosen from formulae (I) and (II), their tautomeric forms, and their addition salts:

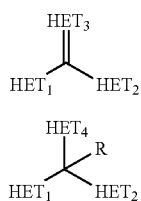

wherein:

R is chosen from hydrogen, halogen; hydroxyl; alkoxy, and alkylthio; and $HET_1$, $HET_2$, $HET_3$ and $HET_4$, which may be identical or different, are chosen from heterocycle, observing a pause time, and rinsing said fibers.

23. A method according to claim 22, wherein said keratin fibers are human keratin fibers.

24. A method according to claim 23, wherein said human keratin fibers are hair.

25. A method according to claim 22, wherein the pause time observed ranges from about 3 to about 50 minutes.

26. A method according to claim 25, wherein the pause time observed ranges from about 5 to about 30 minutes.

27. A method for dyeing keratin fibers comprising applying to said fibers, at least one dye chosen from either formula (II), its tautomeric forms, and its addition salts, as recited in claim 1, or formula (I), its tautomeric forms, and its addition salts, as recited in claim 1, and at least one oxidation base and optionally one at least one coupler, and developing with at least one oxidizing agent a color at acid, neutral or alkaline pH.

28. A method according to claim 27, wherein said keratin fibers are chosen from human keratin fibers.

29. A method according to claim 28, wherein said human keratin fibers are chosen from hair.

30. A method according to claim 27, wherein said at least one oxidizing agent is chosen from hydrogen peroxide, carbamide peroxide, alkaline metal bromates, persalts, peracids, and oxidase enzymes.

31. A method according to claim 30, wherein said persalts are chosen from perborates and persulphates, and said oxidase enzymes are chosen from peroxydases, oxydoreductases with 2 electrons, and oxygenases with 4 electrons.

32. A method according to claim 31, wherein said oxydoreductases with 2 electrons are chosen from uricases and wherein said oxygenases with 4 electrons are chosen from laccases.

33. A device or kit with at least two separate compartments, comprising a first compartment containing a dyeing composition comprising at least one dye chosen from either formula (II), its tautomeric forms, and is addition salts, as recited in claim 1, or formula (I), its tautomeric forms, and its addition salts, as recited in claim 1, at least one oxidation base, and optionally at least one coupler, and a second compartment containing an oxidizing composition.

* * * * *

UNITED STATES PATENT AND TRADEMARK OFFICE
CERTIFICATE OF CORRECTION

PATENT NO.         : 7,211,118 B2
APPLICATION NO. : 10/746497
DATED              : May 1, 2007
INVENTOR(S)        : Frédéric Guerin et al.

It is certified that error appears in the above-identified patent and that said Letters Patent is hereby corrected as shown below:

In claim 4, column 17, line 34, "dehydroquinoleine," should read --dehydroquinoline,--.

In claim 33, column 20, line 32, "is" should read --its--.

Signed and Sealed this

Fourteenth Day of August, 2007

JON W. DUDAS
*Director of the United States Patent and Trademark Office*